United States Patent [19]

Fletcher

[11] Patent Number: 4,933,448

[45] Date of Patent: Jun. 12, 1990

[54] CHROMOGENIC LACTONE COMPOUNDS OF BENZOPYRANO-2H-PYRAZOLES

[75] Inventor: Ian J. Fletcher, Magden, Switzerland

[73] Assignee: Ciba-Geigy Corporation, Ardsley, N.Y.

[21] Appl. No.: 343,094

[22] Filed: Apr. 25, 1989

[30] Foreign Application Priority Data

Apr. 27, 1988 [CH] Switzerland ................ 1568/88

[51] Int. Cl.⁵ .................... C07D 491/02; C09B 57/00
[52] U.S. Cl. ................................. 544/140; 546/15; 548/370
[58] Field of Search .................... 544/140; 546/15; 548/370

[56] References Cited

U.S. PATENT DOCUMENTS

| | | |
|---|---|---|
| 3,837,889 | 9/1974 | Hughes et al. ............... 546/15 X |
| 3,974,175 | 8/1976 | Garner et al. ............... 548/370 |
| 4,007,195 | 2/1977 | Garner et al. ............... 546/15 |
| 4,011,237 | 3/1977 | Petitpierre et al. ........ 260/310 R |
| 4,039,557 | 8/1977 | Garner et al. ............... 548/370 |
| 4,410,708 | 10/1983 | Yahagi et al. ............... 546/15 X |

FOREIGN PATENT DOCUMENTS

| | | |
|---|---|---|
| 2441594 | 3/1975 | Fed. Rep. of Germany ...... 548/370 |
| 1264636 | 2/1972 | United Kingdom . |

*Primary Examiner*—Mary C. Lee
*Assistant Examiner*—Catherine S. Kilby Scalzo
*Attorney, Agent, or Firm*—George R. Dohmann; Kevin T. Mansfield

[57] ABSTRACT

Chromogenic lactone compounds of benzopyrano-2H-pyrazoles of the formula

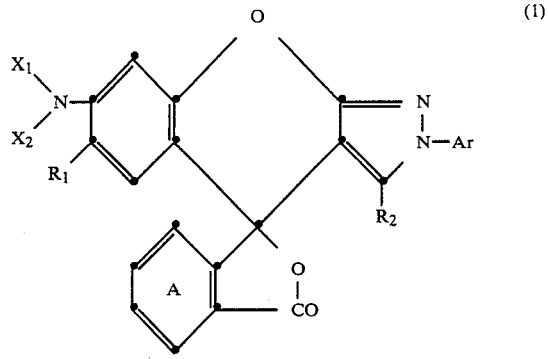

in which
Ar is an aryl radical which is unsubstituted or substituted by halogen, nitro, cyano, lower alkyl, lower alkoxy, lower alkylthio, lower alkoxycarbonyl, trifluoromethyl, phenoxy, phenylthio or $-NX_3X_4$,
$R_1$ is hydrogen, lower alkyl or lower alkoxy,
$R_2$ is lower alkyl, phenyl, or phenyl which is substituted by halogen, lower alkyl or lower alkoxy, and
$X_1$, $X_2$, $X_3$ and $X_4$, independently of one another, are each hydrogen, alkyl which is unsubstituted or substituted by halogen, hydroxyl, cyano, tetrahydrofuryl or lower alkoxy, or are acyl, cycloalkyl, or aralkyl or aryl, each of which is unsubstituted or substituted by halogen, cyano, nitro, trifluoromethyl, lower alkyl, lower alkoxy or lower alkoxycarbonyl, or the substituent pairs ($X_1$ and $X_2$) and ($X_3$ and $X_4$), in each case together with the common nitrogen atom, are a 5- or 6-membered, preferably saturated heterocyclic radical, and in which the ring A is unsubstituted or substituted by halogen, nitro, lower alkyl, lower alkoxy, lower alkylthio, lower alkoxycarbonyl, amino, mono(lower alkyl)amino or di(lower alkyl)amino.

These novel lactone compounds are particularly suitable as color formers in pressure-sensitive or heat-sensitive recording materials, and give intense yellow, orange or red colorations.

12 Claims, No Drawings

CHROMOGENIC LACTONE COMPOUNDS OF BENZOPYRANO-2H-PYRAZOLES

The invention relates to chromogenic lactone compounds of benzopyrano-2H-pyrazole compounds, a process for their preparation, and their use as colour formers in pressure-sensitive or heat-sensitive recording materials.

The benzopyrano-2H-pyrazole lactone compounds according to the invention conform to the general formula

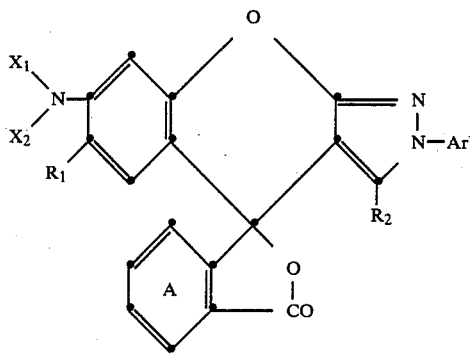

in which

Ar is an aryl radical which is unsubstituted or substituted by halogen, nitro, cyano, lower alkyl, lower alkoxy, lower alkylthio, lower alkoxycarbonyl, trifluoromethyl, phenoxy, phenylthio or $-NX_3X_4$, $R_1$ is hydrogen, halogen, lower alkyl or lower alkoxy, $R_2$ is lower alkyl, phenyl, or phenyl which is substituted by halogen, lower alkyl or lower alkoxy, and $X_1$, $X_2$, $X_3$ and $X_4$, independently of one another, are each hydrogen, alkyl having a maximum of 12 carbon atoms which is unsubstituted or substituted by halogen, hydroxyl, cyano, tetrahydrofuryl or lower alkoxy, or are acyl having 1 to 12 carbon atoms, cycloalkyl having 5 to 10 carbon atoms, or aralkyl or aryl, each of which is unsubstituted or substituted by halogen, cyano, nitro, trifluoromethyl, lower alkyl, lower alkoxy or lower alkoxycarbonyl, or the substituent pairs ($X_1$ and $X_2$) and ($X_3$ and $X_4$), in each case together with the common nitrogen atom, are a 5- or 6-membered, preferably saturated, heterocyclic radical, and in which the ring A is unsubstituted or substituted by halogen, nitro, lower alkyl, lower alkoxy, lower alkylthio, lower alkoxycarbonyl, amino, mono (lower alkyl)amino or di(lower alkyl)amino.

In the definition of the radicals of the lactone compounds, lower alkyl, lower alkoxy and lower alkylthio are groups or group constituents which have 1 to 5, in particular 1 to 3, carbon atoms. Examples of such groups are methyl, ethyl, n-propyl, isopropyl, n-butyl, sec-butyl, tert-butyl, amyl, isoamyl or tert-amyl, or methoxy, ethoxy, isopropoxy, isobutoxy or tert-butoxy, or methylthio, ethylthio, propylthio or butylthio.

Halogen is, for example, fluorine, bromine or, preferably, chlorine. Acyl is particularly formyl, lower alkylcarbonyl, for example acetyl or propionyl, or benzoyl. Further acyl radicals may be lower alkylsulfonyl, for example methylsulfonyl or ethylsulfonyl, or phenylsulfonyl. Benzoyl and phenylsulfonyl may be substituted by halogen, methyl, methoxy or ethoxy.

$R_1$ is preferably methyl, methoxy, bromine, chlorine or, in particular, hydrogen.

$R_2$ is preferably lower alkyl or, in particular, methyl. Optionally substituted phenyl $R_2$ can be phenyl, tolyl, xylyl, chlorophenyl, methoxyphenyl or carbomethoxyphenyl.

The aryl radical Ar is expediently diphenyl, naphthyl and, primarily, phenyl. Ar is preferably a phenyl or naphthyl radical, each of which is unsubstituted or substituted by halogen, nitro, lower alkyl, lower alkoxy, lower alkoxycarbonyl, phenoxy or $-NX_3X_4$.

If the substituents $X_1$, $X_2$, $X_3$ and $X_4$ are alkyl groups, they may be straight-chain or branched. Examples of such alkyl radicals are methyl, ethyl, n-propyl, isopropyl, n-butyl, sec-butyl, tert-butyl, amyl, isoamyl, n-hexyl, 2-ethylhexyl, n-heptyl, n-octyl, isooctyl, n-nonyl, isononyl or n-dodecyl.

If the alkyl radicals in $X_1$, $X_2$, $X_3$ and $X_4$ are substituted, they are, in particular, cyanoalkyl, haloalkyl, hydroxyalkyl or alkoxyalkyl, in each case preferably with a total of 2 to 6 carbon atoms, for example β-cyanoethyl, β-chloroethyl, γ-chloropropyl, β-hydroxyethyl, γ-hydroxypropyl, β-methoxyethyl, β-ethoxyethyl or γ-methoxypropyl, or alternatively tetrahydrofurfuryl.

Examples of cycloalkyl radicals X are cyclopentyl, cycloheptyl or, preferably, cyclohexyl. The cycloalkyl radicals may contain one or more $C_1$-$C_4$alkyl radicals, preferably methyl groups, and have a total of 5 to 10 carbon atoms.

Aralkyl $X_1$, $X_2$, $X_3$ and $X_4$ may be phenethyl, phenylisopropyl or, in particular, benzyl. Aryl radicals X are, in particular, naphthyl or, primarily, phenyl.

Preferred substituents in the aralkyl and aryl group of the X radicals are, for example, halogen, cyano, methyl, trifluoromethyl, methoxy or carbomethoxy. Examples of araliphatic and aromatic radicals of this type are methylbenzyl, 2,4- or 2,5-dimethylbenzyl, chlorobenzyl, dichlorobenzyl, cyanobenzyl, tolyl, xylyl, chlorophenyl, methoxyphenyl, trifluoromethylphenyl, 2,6-dimethylphenyl or carbomethoxyphenyl.

If the substituent pairs ($X_1$ and $X_2$) and ($X_3$ and $X_4$), in each case together with the common nitrogen atom, are a heterocyclic radical, this is, for example, pyrrolidino, piperidino, pipecolino, morpholino, thiomorpholino or piperazino, for example N-methylpiperazino. Preferred saturated heterocyclic radicals for $-NX_1X_2$ and $-NX_3X_4$ are pyrrolidino, piperidino or morpholino.

The substituents $X_1$ and $X_2$ are preferably cyclohexyl, tolyl, benzyl, cyano(lower alkyl), for example β-cyanoethyl, or, primarily, lower alkyl, for example methyl, ethyl, n-propyl, isopropyl, n-butyl or isoamyl. $-NX_1X_2$ is preferably also pyrrolidinyl or N-(lower alkyl)-N-tetrahydrofurfurylamino.

The substituents $X_3$ and $X_4$ are preferably hydrogen, $C_1$-$C_8$alkyl, cyclohexyl, phenyl, benzyl, or phenyl or benzyl which is substituted by halogen, methyl, methoxy, carbomethoxy or trifluoromethyl. $-NX_3X_4$ is preferably also acetylamino, propionylamino or benzoylamino.

The ring A is advantageously not further substituted. If it contains substituents, it is primarily substituted by halogen, nitro, lower alkyl, lower alkoxycarbonyl or di(lower alkyl)amino. Ring A is preferably unsubstituted or substituted by halogen.

Benzopyrano-2H-pyrazole lactone compounds of practical importance conform to the formula

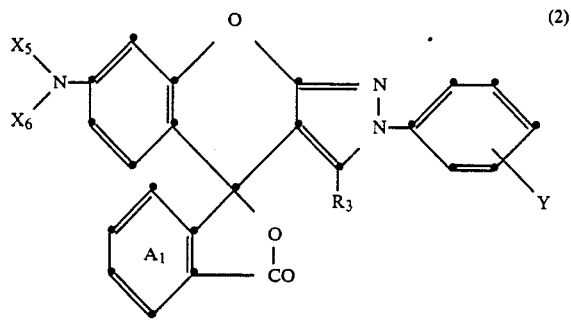

(2)

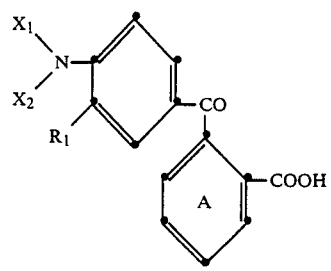

(4)

in which

R$_3$ is lower alkyl or phenyl,

Y is hydrogen, halogen, nitro, lower alkyl, lower alkoxy, phenoxy or —NX$_7$X$_8$, X$_5$, X$_6$, X$_7$ and X$_8$, independently of one another, are each C$_1$–C$_8$alkyl, C$_5$–C$_6$cycloalkyl or benzyl or phenyl, each of which is unsubstituted or substituted by halogen, lower alkyl, lower alkoxy or lower alkoxycarbonyl, and X$_8$ is alternatively hydrogen, or the substituent pairs (X$_5$ and X$_6$) and (X$_7$ and X$_8$), independently of one another and in each case together with the respective common nitrogen atom, are pyrrolidino, piperidino or morpholino, and the ring A$_1$ is unsubstituted or substituted by halogen, lower alkyl, lower alkoxycarbonyl or di(lower alkyl)amino.

Of the lactone compounds of the formula (2), those are particularly preferred in which R$_3$ is lower alkyl, in particular methyl, and Y is hydrogen, halogen, nitro, methyl or di(lower alkyl)amino, and the ring A$_1$ is unsubstituted.

Of particular interest are benzopyrano-2H-pyrazole lactone compounds of the formula

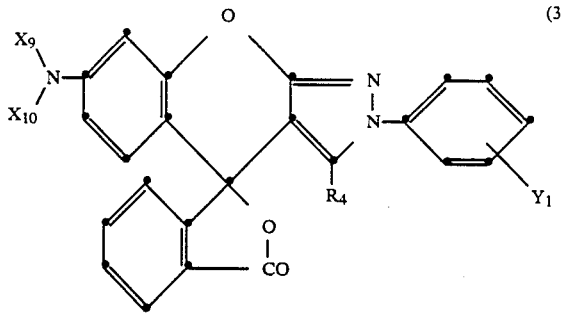

(3)

in which

R$_4$ is methyl or phenyl,

Y$_1$ is hydrogen, chlorine, nitro, methyl, carbomethoxy or di(lower alkyl)amino, X$_9$ is C$_1$–C$_6$alkyl, cyclohexyl, benzyl, phenyl, or phenyl which is substituted by methyl or chlorine, and X$_{10}$ is C$_1$–C$_6$alkyl.

Very particularly preferred lactone compounds are those of the formula (3) in which X$_9$ and X$_{10}$ are C$_1$–C$_5$alkyl, R$_4$ is methyl and Y$_1$ is hydrogen, chlorine, nitro, methyl or dimethylamino.

The lactone compounds of the formulae (1) to (3) according to the invention are prepared by reacting a keto acid compound of the formula 0134 with a pyrazolone compound of the formula

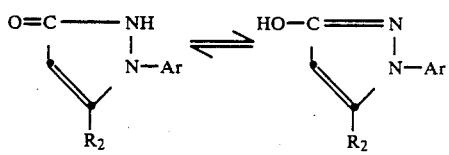

(5)

in which A, Ar, R$_1$, R$_2$, X$_1$ and X$_2$ are as defined above.

The reaction is expediently carried out by reacting the reaction components in the presence of an acidic condensation agent at a temperature of from 20° to 140° C. Examples of condensation agents of this type are acetic anhydride, zinc chloride, aluminium chloride, sulfuric acid, phosphoric acid and phosphorus oxychloride.

The end product of the formula (1) is generally isolated in a known manner by adjusting the pH of the reaction mixture to at least 6, preferably 7 to 14, for example using alkalis, for example alkali metal hydroxides, ammonia, alkali metal carbonates or alkali metal bicarbonates, and separating off, washing and drying the product formed, or by treatment with suitable organic solvents, for example methanol, isopropanol, ligroin, benzene, chlorobenzene, toluene or xylene.

The majority of the starting materials of the formula (4) are known. They are obtained by reacting the acid anhydride of the formula

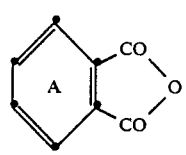

(6)

with a hydroxyl compound of the formula

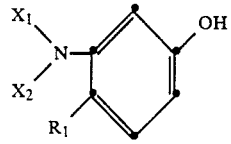

(7)

preferably in an organic solvent, for example benzene, toluene, xylene or chlorobenzene. In the formulae (6) and (7), A, R$_1$, X$_1$ and X$_x$ have the definition indicated.

Some of the starting materials of the formula (5) are likewise known. They can be prepared, for example, by the method of C. Venturello, and R. D'Aloisio, Synthesis 1979, 283, from 2-arylazo-2,5-dimethyl-3-oxo-2,3dihydrofurans in a strongly acidic medium in the presence of acetic acid and concentrated hydrochloric acid and with formation of corresponding N-acetyl derivatives as intermediates. A further preparative method for starting materials of the formula (5) is described in U.S. Pat. No. 2,227.654.

Compounds of the formula (1) in which Ar is an aryl radical which is substituted by —NX$_3$X$_4$ also be prepared by reducing a compound of the formula (1) in which Ar is a nitroaryl radical in a customary manner to form the aminoaryl group, and then reacting the product with a reactive ester of an alkyl alcohol or benzyl alcohol and of an inorganic or organic acid or alternatively with a reactive, functional derivative of a carboxylic acid, in particular fatty acid halides or fatty acid anhydrides, for example acetyl chloride, acetyl bromide or acetic anhydride. Examples of the abovementioned reactive esters are methyl, ethyl, n-propyl, n-butyl or benzyl esters of hydrochloric acid, hydrobromic acid or hydroiodic acid, dimethyl sulfate or diethyl sulfate.

The benzopyrano-2H-pyrazole lactone compounds of the formulae (1) to (3) are normally colourless or at most pale coloured. When these colour formers are brought into contact with a developer, preferably an acidic developer, i.e. an electron acceptor, intense yellow, orange or red colour shades which are particularly light-fast and sublimation-fast are produced immediately, depending on the meaning of Ar; in particular of Y, and on the developer used.

The lactone compounds of the formulae (1) to (3) are also very valuable when mixed with one or more other known colour formers, for example 3,3-(bisaminophenyl)phthalides, 3-indolyl-3-aminophenylazaphthalides, (3,3-bisindolyl)phthalides, 3-aminofluorans, 3-dialkylamino-7-dibenzylaminofluorans, 3-dialkylamino-6-methyl-7-arylaminofluorans, leucoauramines, spiropyrans, spirodipyrans, chromenoindoles, phenoxazines, phenothiazines, quinazolines, rhodamine lactams, carbazolylmethanes or other triarylmethane leuco dyes, in order to produce grey or black dyeings.

The lactone compounds of the formulae (1) to (3) exhibit an excellent colour intensity both on activated clays and on phenolic substrates. They are particularly suitable as fast-developing colour formers for use in a heat-sensitive or, in particular, pressure-sensitive recording material, which can be either a copying material or a recording material. They are distinguished by the fact they they are pH stable, light-fast and readily soluble in capsule oils. After exposure in a CB sheet, they have a low decrease in the colour strength (CB deactivation).

A pressure-sensitive material comprises, for example, at least one pair of sheets which contain at least one colour former of the formulae (1) to (3) dissolved in an organic solvent, and an electron acceptor as developer.

Typical examples of such developers are activated clay substances, such as attapulgite, acid clay, bentonite, montmorillonite, activated clay, for example acid-activated bentonite or montmorillonite, furthermore zeolite, halloysite, silicon dioxide, aluminium oxide, aluminium sulfate, aluminium phosphate, hydrated zirconium dioxide, zinc chloride, zinc nitrate, activated kaolin or any other clay. Developers which can be used are also acidic, organic compounds, for example optionally ring-substituted phenols, resorcinols, salicylic acids, for example 3,5-bis($\alpha,\alpha$-dimethylbenzyl)salicyclic or 3,5-bis-($\alpha$-methylbenzyl)salicylic acid, or salicyl acid esters and metal salts thereof, for example zinc salts, and an acidic, polymeric material, for example a phenolic polymer, an alkylphenolacetylene resin, a maleic acid/colophonium resin or a partially or fully hydrolysed polymer of maleic anhydride with styrene, ethylene or vinyl methyl ether, or carboxymethylene. It is also possible to use mixtures of the monomeric and polymeric compound mentioned. Particularly preferred developers are acid-activated bentonite, zinc salicylates or the products of the condensation of p-substituted phenols with formaldehyde. The latter could also have been modified using zinc.

In addition, the developers can also be employed in a mixture with pigments or further auxiliaries which are unreactive or less reactive per se, such as silica gel or UV absorbers, for example 2-(2'-hydroxyphenyl)benzotriazoles. Examples of such pigments are: talcum, titanium dioxide, aluminium oxide, aluminium hydroxide, zinc oxide, chalk, clays such as kaolin, and organic pigments, for example urea-formaldehyde condensates (BET surface area 2–75 m$^2$/g) or melamine-formaldehyde condensation products.

The colour formers give a coloured mark at the points at which they come into contact with the electron acceptor. In order to prevent premature activation of the colour formers present in the pressure-sensitive recording material, they are generally separated from the electron acceptor. This can expediently be achieved by incorporating the colour formers into foam-like, sponge-like or honeycomb-like structures. The colour formers are preferably included in microcapsules, which can generally be broken by means of pressure.

When the capsules are broken by pressure, for example by means of a pencil, the colour former solution is transferred onto an adjacent sheet which is coated with an electron acceptor, which causes a coloured point to be produced. The colour results from the dye formed during this operation, this dye absorbing in the visible region of the electromagnetic spectrum.

The colour formers are preferably encapsulated in the form of solutions in organic solvents. Examples of suitable solvents are preferably non-volatile solvents, for example halogenated paraffin or diphenyl, such as chlorinated paraffin, monochlorodiphenyl or trichlorodiphenyl, furthermore tricresyl phosphate, di-n-butyl phthalate, dioctyl phthalate, trichlorobenzene, trichloroethyl phosphate, aromatic ethers, such as benzyl phenyl ether, hydrocarbon oils, such as paraffin or kerosine, for example isopropyl-, isobutyl-, sec-butyl- or tert-butyl-alkylated derivatives of diphenyl, naphthalene or terphenyl, dibenzyltoluene, partially hydrogenated terphenyl, mono- to tetra-C$_1$–C$_3$-alkylated diphenylalkanes, dodecylbenzene, benzylated xylenes, or further chlorinated or hydrogenated, condensed, aromatic hydrocarbons. Mixtures of different solvents, in particular mixtures of paraffin oils or kerosine and diisopropylnaphthaline or partially hydrogenated terphenyl, are frequently employed in order to achieve optimum solubility for the colour formation, rapid and intense colouration and a vicosity which is favourable for the microencapsulation.

The capsule walls can be formed uniformly around the droplets of the colour former solution by coacervation forces, the encapsulation material being described, for example, in U.S. Pat. No. 2,800,457. The capsules can preferably also be formed from an amino plastic or modified amino plastic by polycondensation, as described in British Pat. Nos. 989,264, 1,156,725, 1,301,052 and 1,355,124. Microcapsules formed by interface polymerisation, for example capsules of polyester, polycarbonate, polysulfonamide, polysulfonate, but particularly of polyamide or polyurethane, are likewise suitable.

The microcapsules containing colour formers of the formulae (1) to (3) can be used to produce pressure-sensitive copying materials of a very wide variety of known types. The various systems differ essentially from one another through the arrangement of the capsules, the colour reactants and through the substrate material.

A preferred arrangement is one in which the encapsulated colour former is present in the form of a coating on the rear of a transfer sheet, and the electron acceptor is present in the form of a coating on the front of a receiver sheet.

Another arrangement of the constituents comprises the microcapsules containing the colour former and the developer being present in or on the same sheet in the form of one or more individual coatings or in the paper pulp.

The capsules are preferably fixed on the substrate by means of a suitable binder. Since the preferred substrate material is paper, this binder is generally a paper coating agent, such as gum arabic, polyvinyl alcohol, hydroxymethylcellulose, casein, methylcellulose, dextrin, starch, starch derivatives or polymer lattices. The latter are, for example, butadienestyrene copolymers or acrylic homopolymers or copolymers.

The papers used are not only standard papers made from cellulose fibers, but also papers in which the cellulose fibres have been replaced (partially or fully) by fibres made from synthetic polymers.

The self-copying material preferably also contains a capsule-free coating containing the lactone compound, and a colour-developing coating which contains, as colour developer, at least one inorganic metal salt, in particular halides or nitrates of a polyvalent metal, for example zinc chloride, tin chloride, zinc nitrate or mixtures thereof.

The compounds of the formulae (1) to (3) can also be used as colour formers in a thermoreactive recording material. This generally contains at least one coating substrate, a colour former, an electron acceptor and possibly also a binder and/or wax. If desired, activators or sensitizers can also be present in the recording material.

Thermoreactive recording systems include, for example, thermosensitive recording and copying materials and papers. These systems are used, for example, for recording information, for example in electronic calculators, teleprinters, telex machines or in recording instruments and measuring instruments, for example electrocardiographs. The image production (marking) can also take place manually using a heated pen. Laser beams are a further piece of equipment for producing markings by means of heat.

The thermoreactive recording material can be constructed so that the colour former is dissolved or dispersed in a binder coating and the developer is dissolved or dispersed in the binder in a second coating. Another possibility is for the colour former and the developer to be dispersed in one coating. The binder is softened in specific areas by means of heat, and the colour former comes into contact with the electron acceptor at these points at which heat is used, and the desired colour develops immediately.

Suitable developers are the same electron acceptors as are used in pressure-sensitive papers. Examples of developers are the abovementioned clay minerals and phenolic resins, or alternatively phenolic compounds as described, for example, in German Pat. No. 1,251,348, for example 4-tertbutylphenol, 4-phenylphenol, methylene-bis(p-phenylphenol), 4-hydroxydiphenyl ether, α-naphthol, β-naphthol, methyl or benzyl 4-hydroxybenzoates, 4-hydroxydiphenyl sulfone, 2,4-dihydroxydiphenylsulfone, 4'-hydroxy-4-methyldiphenyl sulfone, 4'-hydroxy-4-isopropoxydiphenyl sulfone, 4-hydroxyacetophenone, 2,2'-dihydroxydiphenyl, 4,4'-cyclohexylidenediphenol, 4,4'-isopropylidenediphenol, 4,4'-isopropylidenebis(2-methylphenol), an antipyrine complex of zinc thiocyanate, a pyridine complex of zinc thiocyanate, 4,4-bis(4-hydroxyphenyl)valeric acid, hydroquinone, pyrogallol, phloroglucine, p-, m- and o-hydroxybenzoic acid, gallic acid, 1-hydroxy-2-naphthoic acid and boric acid, or organic, preferably aliphatic, dicarboxylic acids, for example tartaric acid, oxalic acid, maleic acid, citric acid, citraconic acid or succinic acid.

The production of the thermoreactive recording material is preferably carried out using meltable, film-forming binders. These binders are normally water-soluble, whereas the lactone compounds and the developer are sparingly soluble or insoluble in water. The binder should be capable of dispersing and fixing the colour former and the developer at room temperature.

Under the action of heat, the binder softens or melts, meaning that the colour former comes into contact with the developer, enabling a colour to form. Water-soluble or at least water-swellable binders are, for example, hydrophilic polymers, such as polyvinyl alcohol, polyacrylic acid, hydroxyethylcellulose, methylcellulose, carboxymethylcellulose, polyacrylamide, polyvinylpyrrolidone, carboxylated butadiene-styrene copolymers, gelatins, starch or etherified maize starch.

If the colour former and the developer are present in two separate coatings, water-insoluble binders, i.e. binders which are soluble in non-polar or only slightly polar solvents, for example natural rubber, synthetic rubber, chlorinated rubber, polystyrene, styrene-butadiene copolymers, polymethyl acrylates, ethylcellulose, nitrocellulose and polyvinylcarbazole, can be used. The preferred arrangement, however, is that in which the colour former and the developer are present in one coating in a water-soluble binder.

The thermoreactive coatings may contain further additives. In order to improve the degree of whiteness, in order to simplify printing of the papers and in order to prevent the heated pen sticking fast, these coatings can contain, for example, talcum, titanium dioxide, zinc oxide, aluminium hydroxide, calcium carbonate (for example chalk), clays or alternatively organic pigments, for example urea-formaldehyde polymers. In order to cause the colour to be formed only within a limited temperature range, substances, for example urea, thiourea, diphenylthiourea, acetamide, acetanilide, benzenesulfanilide, bis-stearoylethylenediamide, stearamide, phthalic anhydride, metal stearates, for example zinc stearate, phthalonitrile, dimethyl terephthalate, dibenzyl terephthalate or other corresponding, meltable products which induce simultaneous melting of the colour former and of the developer can be added. Thermographic recording materials preferably contain waxes, for example carnauba wax, montan wax, paraffin wax, polyethylene wax, condensates of higher fatty amides and formaldehydes, and condensates of higher fatty acids and ethylenediamine.

A further application of the compounds of the formulae (1) to (3) is the production of a colour image by means of photocurable microcapsules, as described, for example, in German Offenlegungsschrift No. 3,247,488.

In the examples below, the percentages indicated relate to the weight, unless stated otherwise. Parts denote parts by weight.

EXAMPLE 1

15.7 g of 2-hydroxy-4-diethylamino-2'-carboxybenzophenone are dissolved at room temperature in 50 ml of sulfuric acid (98 %) with stirring. 8.7 g of 1-phenyl-5-methylpyrazol-(3)-one are introduced in portions into this solution, after which the mixture is stirred at room temperature overnight (10–12 hours). The reaction mixture is poured into ice water and rendered alkaline using concentrated ammonia water. The product which precipitates is filtered off, washed with water and dried in vacuo at 60°–70° C. 23 g of a crude product which, after recrystallization from ligroin/toluene, gives 15.2 g of a compound of the formula

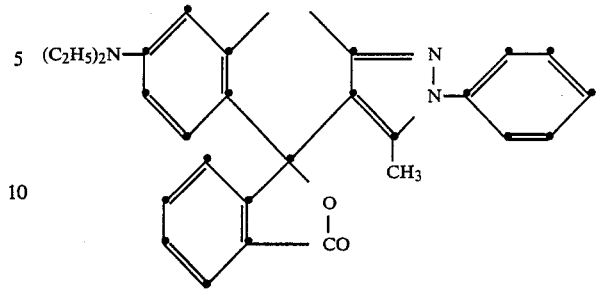

having a melting point of 235°–237° C. are obtained. On acid clay, this lactone compound immediately gives an intense and light-fast orange colouration.

If the 2-hydroxy-4-diethylamino-2'-carboxybenzophenone in Example 1 is replaced by the equivalent amount of
  (a) 2-hydroxy-4-diethylamino-2'-carboxy-3', 4'-5', 6'-tetrachlorobenzophenone or
  (b) 2-hydroxy-4-diethylamino-2'-carboxy-4'/5'-tert-butylbenzophenone and the procedure as in the example is followed, the lactone compounds of the formulae (12) and (13), which give an intense orange colour on acid clay, are obtained.

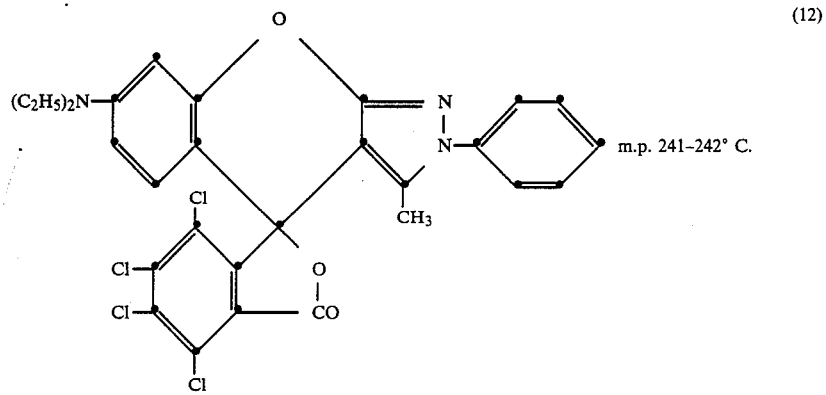

m.p. 241–242° C.

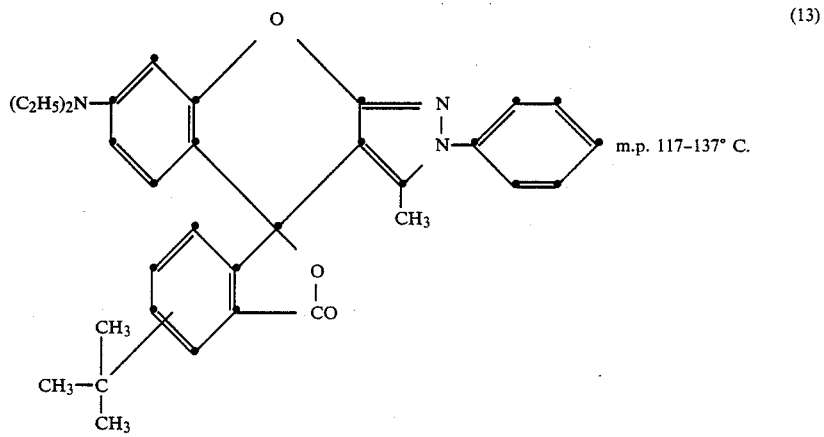

m.p. 117–137° C.

In the same manner as described in Example 1, the lactone compounds of the formula which are listed in the table below and give the colour indiated on acid clay, are obtained using the appropriate starting material.

TABLE

| Ex. | Z | Ar' | R'₄ | m.p./°C. | Colour |
|---|---|---|---|---|---|
| 2 | —N(C₂H₅)₂ | 4-CH₃-phenyl | —CH₃ | 113–125 | orange |
| 3 | —N(C₂H₅)₂ | 4-Cl-phenyl | —CH₃ | 115–128 | orange |
| 4 | —N(C₄H₉)₂ | phenyl | —CH₃ | 87–90 | orange |
| 5 | —N(C₂H₅)₂ | 2-Cl-phenyl | —CH₃ | 195–202 | yellow |
| 6 | —N(C₂H₅)₂ | 4-NO₂-phenyl | —CH₃ | 198–200 | red |
| 7 | —N(C₂H₅)₂ | 4-N(CH₃)₂-phenyl | —CH₃ | 131–145 | red |
| 8 | —N(C₂H₅)₂ | 4-COOC₂H₅-phenyl | —CH₃ | 110–115 | orange |
| 9 | —N(C₂H₅)₂ | 3-COOC₂H₅-phenyl | —CH₃ | 110–120 | orange |
| 10 | —N(C₂H₅)₂ | phenyl | phenyl | 120–125 | orange |
| 11 | —N(pyrrolidinyl) | phenyl | —CH₃ | 150–160 | orange |

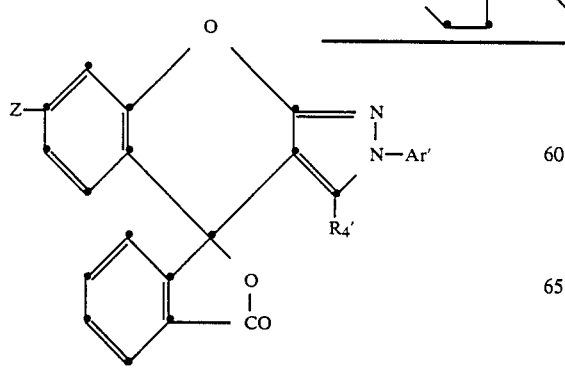

(14)

EXAMPLE 12:

A suspension of 4.7 g of the benzopyrano-2H-pyrazole compound of the formula

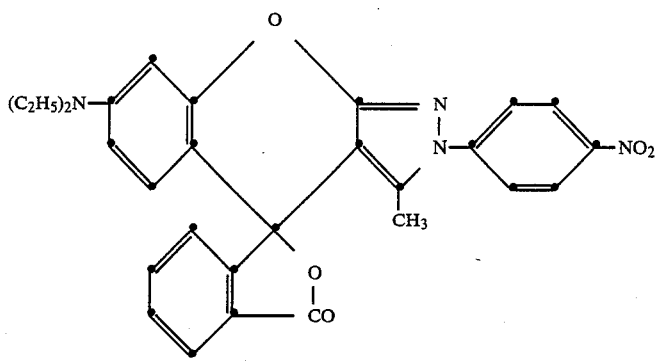
(15)

prepared in accordance with Example 6 in 9.2 ml of water and 27.4 ml of concentrated hydrochloric acid is warmed to 70°–80° C. with stirring. 6.2 g of tin dichloride dihydrate are added in portions to the suspension, the temperature increasing to 90°–92° C. The reduction of the nitrocompound is complete after 2 hours. The mixture is diluted with 150 ml of water, and the reaction product is adjusted to pH 12 using concentrated sodium hydroxide solution. The mixture is stirred at 70°–80° C. for a further 30 minutes, and the product is filtered off. After washing and drying at 80° C. in vacuo, 4.4 g of a compound of the formula

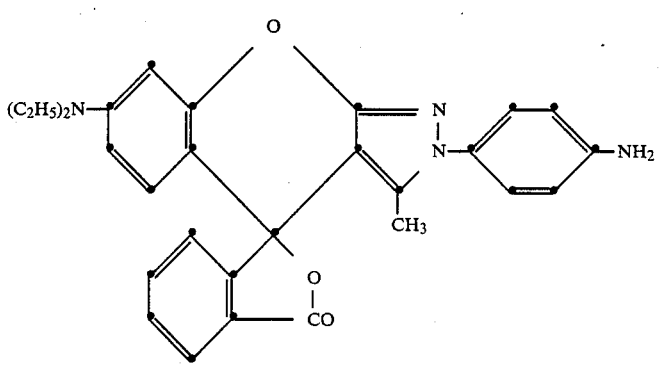
(16)

having a melting point of 255°–260° C. are obtained. (a) 1.3 g of the compound of the formula (16) are heated to 100° C. in 10 ml of acetic anhydride, water is then added, and the mixture is stirred. The product which precipitates is filtered off, washed with water and dried in vacuo at 70° C. After purification on a silica gel column using methylene dichloride, 0.8 g of a compound of the formula

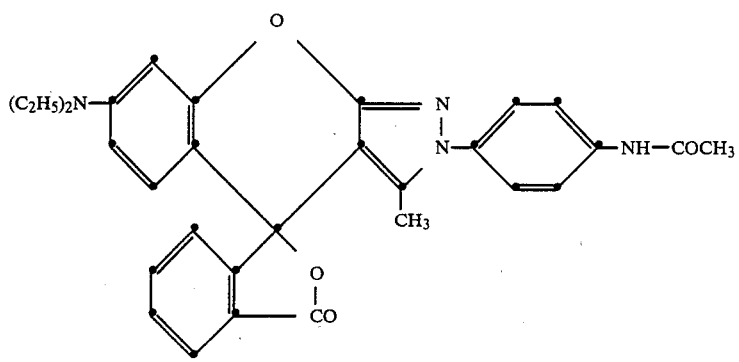
(17)

having a metling point of 176°–182° C. is obtained. This lactone compound gives an intense orange colouration on acid clay. (b) 1.3 g of the compound of the formula (16) are heated at 150°–160° C. for 10 hours in 10 ml of benzyl chloride with stirring, and the excess benzyl chloride is then removed by evaporation. The residue is treated with dilute ammonia solution and filtered off. After washing, drying in vacuo at 60°–70° C. and purification on a silica gel column using methylene dichloride, a compound of the formula

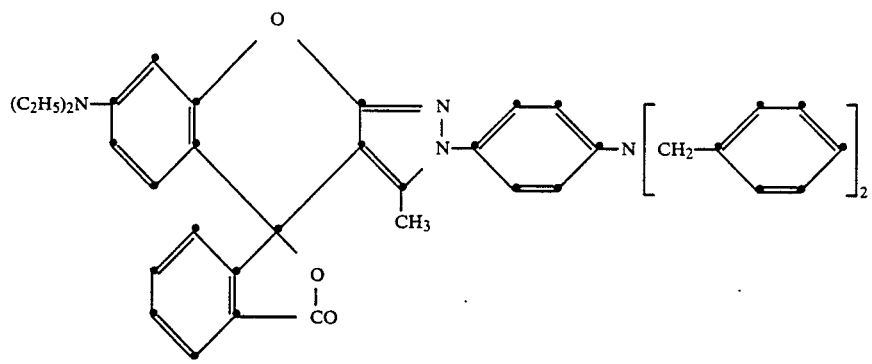

(18)

having a melting point of 188°–200° C. is obtained. This lactone compound gives an intense purple-red colouration on acid clay.

EXAMPLE 13:

Production of a pressure-sensitive copying paper

A solution of 3 g of the lactone compound of the formula (11) in 80 g of diisopropylnaphthalene and 17 g of kerosine is microencapsulated in a manner known per se by coazervation using gelatin and gum arabic, mixed with starch solution and brushed onto a sheet of paper. A second sheet of paper is coated on the front with acid-activated bentonite as colour developer. The first sheet, containing the colour former, and the paper coated with the colour developer are placed one on top of the other with the coatings adjacent. Pressure is exerted on the first sheet by writing by hand or with a typewriter, and an intense orange copy, which has excellent sublimation and light fastness properties, immediately develops on the sheet coated with the developer. Corresponding intense, sublimation- and light-fast copies are also obtained when the colour formers as in Examples 2 to 12 are used.

EXAMPLE 14:

If the lactone compound of the formula (11) in Example 13 is replaced by a mixture of the following composition 1.2 g of 3,3-bis(4'-dimethylaminophenyl)-6-dimethylaminophthalide, 1.2 g of N-butylcarbazol-3-yl-bis(4'-N-methyl-N-phenylaminophenyl)methane 1.2 g of the lactone compound of the formula (11) and 0.4 g of 3,3-bis(N-octyl-2'-methylindol-3'-yl)phthalide and the procedure described in Example 13 is otherwise followed, a pressure-sensitive recording material which gives an intense and light-fast black copy on writing by hand or with a typewriter is thus obtained.

EXAMPLE 15:

1 g of the lactone compound as in Example 6 is dissolved 17 g of toluene. 12 g of polyvinyl acetate, 8 g of calcium carbonate and 2 g of titanium dioxide are added to this solution with stirring. The suspension obtained is diluted with toluene in the weight ratio 1:1 and coated onto a sheet of paper using a 10 μm doctor blade. A second sheet of paper whose underside has been coated at an application weight of 3 g/m² with a mixture comprising 1 part of an amide wax, 1 part of a stearyl wax and 1 part of zinc chloride is placed on this sheet of paper. Pressure is exerted on the upper sheet by writing by hand or with a typewriter, and an intense, sublimation- and light-fast red colour immediately develops on the sheet coated with the colour former.

EXAMPLE 16:

Production of a heat-sensitive recording material 32 g of 4,4'-isopropylidenediphenol (bisphenol A), 3.8 g of the distearylamide of ethylenediamine, 39 g of kaolin, 20 g of an 88 % hydrolysed polyvinyl alcohol and 500 ml of water are ground in a ball mill until the particle size is about 5 μm. 6 g of the lactone compound of the formula (11), 3 g of an 88 % hydrolysed polyvinyl alcohol and 60 ml of water are ground in a second ball mill to a particle size of about 3 μm.

The two dispersions are combined and coated at a dry application weight of 5.5 g/m² onto a paper. An intense orange colour which has excellent sublimation- and light-fastness is obtained by touching the paper with a heated metal pen.

Intense and light-fast colours are also obtained when the colour formers of Examples 2 to 12 are used.

What is claimed is:

1. A chromogenic benzopyrano-2H-pyrazole lactone compound of the formula

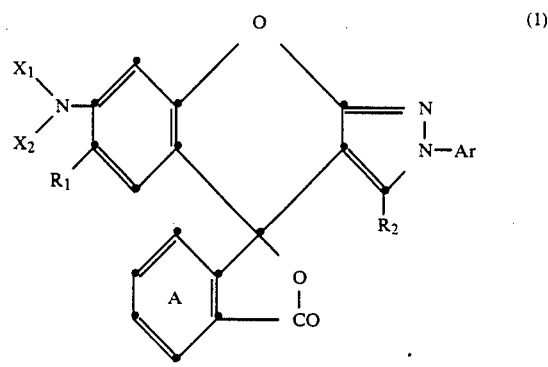

(1)

in which

Ar is aphenyl, diphenyl or naphthyl radical which is unsubstituted or substituted by halogen, nitro, cyano, lower alkyl, lower alkoxy, lower alkylthio, lower alkoxy-carbonyl, trifluoromethyl, phenoxy, phenylthio or $-NX_3X_4$, $R_1$ is hydrogen, halogen, lower alkyl or lower alkoxy, $R_2$ is lower alkyl, phenyl, or phenyl which is substituted by halogen, lower alkyl or lower alkoxy, and $X_1$, $X_2$, $X_3$ and $X_4$, independently of one another, are each hdyrogen, alkyl having 1 to 12 carbon atoms which is unsubstituted or substituted by halogen, hydroxyl, cyano, tetrahydrofuryl or lower alkoxy, or are acyl having 1 to 12 carbon atoms, cycloalkyl having 5 to 10 carbon atoms, or benzyl, phenethyl, phenylisopropyl, phenyl or naphthyl, each of which is unsubstituted or substituted by halogn, cyano, nitro, trifluoromethyl, lower alkyl, lower alkoxy or lower alkoxycarbonyl, or the substituents pairs ($X_1$ and $X_2$) and ($X_3$ and $X_4$), in each case together with the common nitrogen atom, are a pyrrolidino, piperidino, pipecolino, morpholino, thiomorpholino or piperazino radical, and in lower alkylthio, lower alkoxycarbonyl, amino, mono(-lower alkyl)amino or di(lower alkyl)amino.

2. A lactone compound according to claim 1, wherein, the formula (1) $R_1$ is hydrogen, bromine, chlorine, methyl or methoxy.

3. A lactone compound according to claim 1, wherein, in the formula (1) $R_2$ is lower alkyl.

4. A lactone compound according to claim 1, wherein, in the formula (1), Ar is phenyl, naphthyl or phenyl or naphthyl which is substituted by halogen, nitro, lower alkyl, lower alkoxy, lower alkoxycarbonyl, phenoxy or $-NX_3X_4$.

5. A lactone compound according to claim 1, wherein, in the formula (1), $X_1$ and $X_2$ are each lower alkyl, cyclohexyl, tolyl, benzyl or cyano(lower alkyl).

6. A lactone compound according to claim 1, wherein, in the formula (1), the ring A is unsubstituted or substituted by halogen.

7. A lactone compound according to claim 1, of the formula

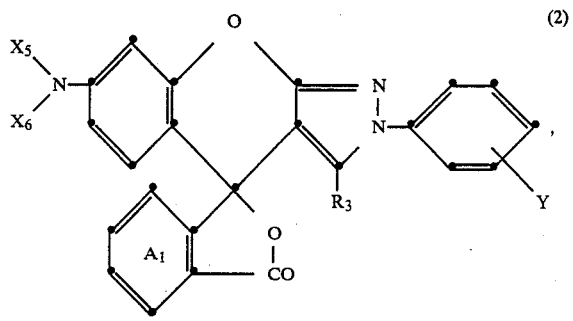

(2)

wherein
$R_3$ is lower alkyl or phenyl,
Y is hydrogen, halogen, nitro, lower alkyl, lower alkoxy, phenoxy or $-NX_7X_8$,
$X_5$, $X_6$, $X_7$ and $X_8$, independently of one another, are each $C_1-C_8$alkyl, $C_5-C_6$cycloalkyl or benzyl or phenyl, each of which is unsubstituted or substituted by halogen, lower alkyl, lower alkoxy or lower alkoxycarbonyl, and $X_8$ is alternatively hydrogen, or the substituent pairs ($X_5$ and $X_6$) and ($X_7$ and $X_8$), independently of one another and in each case together with the respective common nitrogen atom, are pyrrolidino, piperidino or morpholino and the ring $A_1$ is unsubstituted or substituted by halogen, lower alkyl, lower alkoxycarbonyl or di(lower alkyl)amino.

8. A lactone compound according to claim 7, wherein, in the formula (2) $R_3$ is methyl, and
Y is hydrogen, halogen, nitro, methyl or di(lower alkyl)amino, and the ring $A_1$ is unsubstituted.

9. A lactone compound according to claim 1 of the formula

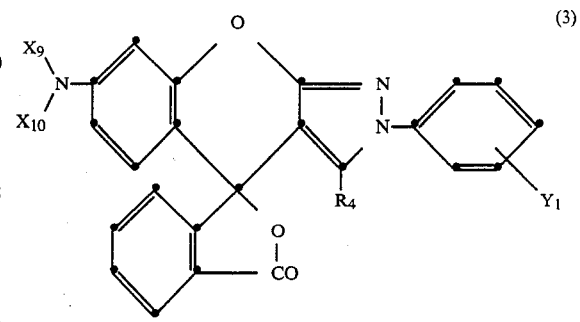

(3)

wherein
$R_4$ is methyl or phenyl,
$Y_1$ is hydrogen, chlorine, nitro, methyl, carbomethoxy or di(lower alkyl)amino
$X_9$ is $C_1-C_6$alkyl, cyclohexyl, benzyl, phenyl, or phenyl which is substituted by methyl or chlorine, and
$X_{10}$ is $C_1-C_6$alkyl.

10. A lactone compound according to claim 9, wherein, in the formula (3), $X_9$ and $X_{10}$ are $C_1-C_5$alkyl, $R_4$ is methyl and $Y_1$ is hydrogen, chlorine, nitro, methyl or dimethylamino.

11. The lactone compound of claim 10, wherein $X_9$ and $X_{10}$ are ethyl and Y: is hydrogen.

12. A process for the preparation of a benzopyrano-2H-pyrazole lactone compound according to claim 1, wherein a keto acid compound of the formula

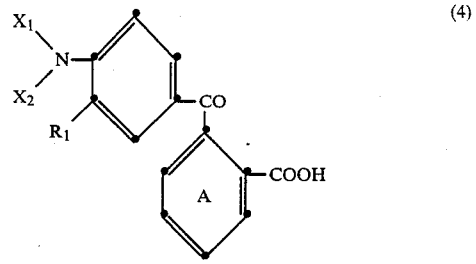

(4)

is reacted with a pyrazolone compound of the formula

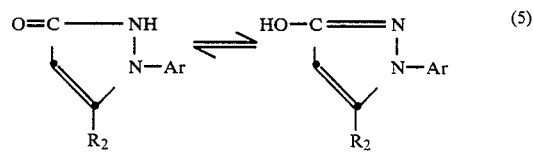

(5)

wherein A, Ar, $R_1$, Rhd 2, $X_1$ and $X_2$ have the definition indicated in claim 1.

* * * * *